(12) United States Patent
Kolb

(10) Patent No.: US 6,926,741 B2
(45) Date of Patent: Aug. 9, 2005

(54) CENTRALIZING CEMENT PLUG WITH COUNTERSINK

(75) Inventor: Eric Kolb, Quincy, MA (US)

(73) Assignee: Depuy Products, Inc., Warsaw, FL (US)

( * ) Notice: Subject to any disclaimer, the term of this patent is extended or adjusted under 35 U.S.C. 154(b) by 67 days.

(21) Appl. No.: 10/056,743

(22) Filed: Jan. 25, 2002

(65) Prior Publication Data

US 2003/0144740 A1 Jul. 31, 2003

(51) Int. Cl.$^7$ ................................................. A61F 2/28
(52) U.S. Cl. ................................................. 623/23.48
(58) Field of Search ............................ 623/23.48, 23.2, 623/95, 23.46, 23.22, 23.23, 23.25, 23.26, 23.27, 23.28; 606/95

(56) References Cited

U.S. PATENT DOCUMENTS

| | | | |
|---|---|---|---|
| 3,793,650 A | | 2/1974 | Ling |
| 5,078,746 A | * | 1/1992 | Garner ................ 623/23.48 |
| 5,092,892 A | | 3/1992 | Ashby |
| 5,108,439 A | * | 4/1992 | Morscher et al. ........ 623/23.46 |
| 5,192,283 A | * | 3/1993 | Ling et al. ............... 606/93 |
| 5,271,737 A | | 12/1993 | Baldwin et al. |
| 5,425,768 A | * | 6/1995 | Carpenter et al. ....... 623/23.48 |
| 5,577,368 A | | 11/1996 | Hamilton et al. |
| 5,658,350 A | * | 8/1997 | Carbone ................ 623/23.19 |
| 5,658,351 A | | 8/1997 | Dudasik |
| 6,017,975 A | | 1/2000 | Saum |
| 6,174,314 B1 | | 1/2001 | Waddell |
| 6,179,842 B1 | * | 1/2001 | Spotorno et al. ............. 606/95 |
| 6,228,090 B1 | | 5/2001 | Waddell |
| 6,228,900 B1 | | 5/2001 | Shen |
| RE37,277 E | | 7/2001 | Baldwin et al. |
| 6,267,785 B1 | | 7/2001 | Masini |

FOREIGN PATENT DOCUMENTS

| | | | | |
|---|---|---|---|---|
| DE | 3314210 | * | 1/1984 | ............. 623/23.48 |
| DE | 3314210 A | | 11/1984 | |
| DE | 4313201 A | | 11/1994 | |
| EP | 0006408 A | | 1/1980 | |
| EP | 0006408 | * | 1/1980 | ............. 623/23.48 |
| EP | 0403028 A | | 12/1990 | |
| EP | 0427444 A | | 5/1991 | |
| EP | 0962198 A | | 12/1999 | |
| EP | 0995411 A | | 4/2000 | |
| EP | 1082948 A | | 3/2001 | |
| FR | 2651118 A | | 3/1991 | |
| FR | 2651118 | * | 3/1991 | ............. 623/23.48 |
| FR | 2758977 A | | 8/1998 | |

* cited by examiner

Primary Examiner—Pedro Philogene

(57) ABSTRACT

A prosthesis (10) including a stem (12) for implantation at least partially within the medullary canal (14) of a long bone (16). The prosthesis (10) further includes a rod (20) operably associated with the stem (12) and a centralizer (22) having an opening (24) for receiving at least a portion of the rod (20). The centralizer (22) has a surface (26) for guiding the rod (20) into the opening (24).

8 Claims, 9 Drawing Sheets

Figure # 3

CENTRALIZING CEMENT PLUG WITH COUNTERSINK

TECHNICAL FIELD OF THE INVENTION

The present invention relates generally to the field of orthopaedics, and more particularly, to an implant for use in arthroplasty.

BACKGROUND OF THE INVENTION

This invention relates to implantible articles and methods for implanting such articles. More particularly, the invention relates to bone prostheses and methods for implanting the same.

There are known to exist many designs for and methods for manufacturing implantible articles, such as bone prosthesis. Such bone prostheses include components of artificial joints, such as elbows, hips, knees and shoulders. An important consideration in the design and manufacture of virtually any implantible bone prosthesis is that the bone prosthesis has adequate fixation when implanted within the body.

Early designs of implantible articles have relied upon the use of cements such as polymethylmethacrylate (PMMA) to anchor the implant. The use of such cements can have some advantages, such as providing a fixation that does not develop free play or does not lead to erosion of adjoining faces post-operatively. Maintaining a load or force at the cement/bone interface assists in providing for good fixation and to prevent motion.

One challenge in the proper positioning of the prosthesis during surgery is the proper position of the stem axially and rotationally. Improper positioning has been shown to limit the patient's range of motion by inducing improper leg length, inadequate lateral stem offset and non-anatomical version of the stem. Inadequate pressurization of the cement within the femoral canal has also been documented as a potential cause of improper cement technique.

Centralization of the stem within the cement mantel is also critical for success. Non-uniform or excessively thin cement mantels can induce high cement stress and subsequent cracks that cause failure at the cement-stem-bone interfaces. The cement debris, due to abrasions, has also been shown to produce excessive third-body wear of polyethylene acetabular components as well as potentially induce osteolytic reactions and bone resorbtions that may lead to stem loosening.

One devise utilized to assist in the centralization of the stem is the use of centralizers or spacers. Centralizers or spacers are provided for fitting to the distal end of a femoral hip replacement stem in order to keep the implant stem away from the internal surface of the cavity of the bone in which this stem is to be inserted.

In the case of stems which are cemented in the bone cavity there is a space between the stem and the internal surface of the cavity of the bone in which the cement is placed. Controlling the position of the stem within the surrounding bone cement mantle is vital to long-term survivability of the replacement joint. Cement can be deposited in the bone cavity and then the stem may be inserted with the centralizer attached to the stem. Alternatively, the centralizer may be inserted into the cavity and the stem later inserted against the centralizer. It is important to try to obtain an even and intact cement mantle around the stem.

In addition to the purpose of the centralizer to properly position the stem, the centralizer may be designed to serve a second purpose, that is to separate the cement from the blood and other body fluids within the medullary canal of the bone. Such separation of cement and medullary canal fluids is exasperated by the more recent use of external pressure to assure the complete filling of the bone cavity with cement.

Known centralizers are in the form of caps which fit over the distal end of the stem and centralizers which are fixed inside of a drilled end of a stem. Centralizers are also known, for example, as described in U.S. Pat. No. 4,658,351 which are of ring form which can have a tapered inner surface corresponding to the tapered surface of the distal stem of the femoral stem on which the centralizer is located.

U.S. Pat. No. 3,793,650 describes a centralizer or spacer which has spring members which extend from the stem for contact with the wall of the bone cavity.

European Patent No. EP0427448B describes a centralizer or spacer in the form of a cap for insertion on the end of a hip stem with fins or wings extending outwardly from the cap which are adapted to fold circumferentially and inwardly toward the body portion of the cap.

Cemented stem systems generally utilize two components distal to the stem, a centralizer and a cement plug. The centralizers usually have fins that protrude into the cement mantle around the stem. During insertion, voids often develop around these fins and these voids are potential sites for crack initiation. The distal tip of the stem is subjected to high levels of stress and therefore voids are of a particular concern. The cement plug's only purpose is to restrict the flow of cement during cement pressurization.

Some designs have attempted to optimize the fin geometry by streamlining it in an effort to reduce the number and size of voids. These designs have failed to eliminate voids entirely.

Other designs have shifted the position of the centralizer to the middle of the stem which experiences lower stress levels. This type of design does not eliminate the voids and since centralization of the stem is not controlled distally, the stem positioning may be compromised.

SUMMARY OF THE INVENTION

According to the present invention, a cement plug having a countersunk proximal end guides a rod. The rod is attached to the distal tip of the stem. The rod is fitted into the center of the endosteal canal without the use of a finned centralizer.

The invention allows for the elimination of cement voids at the distal tip of the cemented hip stem. Voids can contribute to the failure of the cement mantle in subsequent revision surgeries. The proximal end of the cement plug is counterbored. The counterbored proximal end guides a rod. The rod is attached to the distal tip of the stem. The plug is fitted into the center of the endosteal canal as it is inserted.

A rod made of polymethylmethacrylate (PMMA), plastic, metal or other biocompatible material is inserted into the distal tip of the stem prior to insertion in a method similar to a traditional centralizer. During insertion this rod engages with the cement plug and is guided into the center of the canal.

A small hole, slightly larger in diameter than the rod, runs through the entire cement plug. The rod then can pass through the cement plug without pushing it out of position. This permits some malpositioning of the cement plug within the canal. Without this feature, the cement plug would need to be placed at exactly the right position relative to the stem in its fully seated position.

Not having fins allows for smooth cement flow around the distal tip of the stem, reducing the formation of voids in the cement mantle.

The cement plug is countersunk or flared at its proximal end. As the stem is pushed into the canal the flare geometry guides the rod into the center of the canal, creating a uniform cement mantle around the stem.

According to one embodiment of the present invention, there is provided a prosthesis including a stem for implantation at least partially within the medullary canal of a long bone and a rod operably associated with the stem. The prosthesis also includes a centralizer having an aperture for receiving at least a portion of the rod. The centralizer includes a surface for guiding the rod into the aperture.

According to another embodiment of the present invention there is provided a prosthesis for implantation at least partially within the medullary canal of a long bone. The prosthesis includes a stem and a rod. The stem has a first portion and a second portion. The first portion has a cavity. The rod is at least partially fittable within the cavity of the first portion of the stem. The rod has a longitudinal axis. The rod is removable from the stem a first direction along the axis and is restrained within the stem a second direction opposed to the first direction along the axis. The prosthesis also includes a centralizer operably associated with said rod.

According to yet another embodiment of the present invention there is provided a centralizing assembly for use with a stem for implantation at least partially within the medullary canal of a long bone. The centralizing assembly includes a rod and a centralizer. The centralizer has an aperture for receiving at least a portion of the rod. The centralizer includes a surface thereof for guiding the rod into the aperture.

According to another embodiment of the present invention there is provided a rod for use to connect a prosthetic stem with a centralizer for implantation at least partially within the medullary canal of a long bone. The rod is operably associated with the stem. A portion of the rod is made of a resorbable material.

According to yet another embodiment of the present invention there is provided a stem for use with a centralizing assembly. The stem is used for implantation at least partially within the medullary canal of a long bone. The stem has a first portion and a second portion. The first portion has a cavity for cooperation with the centralizing assembly. The centralizing assembly is removable from the stem in a first direction and restrained within the stem a second direction opposed to the first direction.

According to a further embodiment of the present invention, there is provided a method for providing total hip arthroplasty. The method includes the steps of providing total hip arthroplasty including resecting a long bone, opening a medullary canal of the long bone, placing a plug into the canal, inserting cement into the canal, providing a stem having a cavity on the distal end thereof, placing a rod into the cavity, implanting the first end of the stem at least partially within the medullary canal, and connecting the rod with the plug to centralize the stem.

The technical advantages of the present invention include the ability to eliminate the cement voids at the distal tip of the cement which are often caused by the cement needing to pass around the fins found in prior art cement plugs. These voids are potential sites for crack initiation. The distal tip of the stem is subject to high levels of stress and therefore voids are of particular concern.

A further technical advantage of the present invention includes the ability of the centralizer to provide stem centralization referencing the cement restrictor. By centralizing distally, the stem positioning is not compromised in the way that centralizers located in the middle of the stem utilized in prior art centralizers may compromise the positioning of the stem.

Other technical advantages of the present invention will be readily apparent to one skilled in the art from the following figures, descriptions and claims.

BRIEF DESCRIPTION OF THE DRAWINGS

For a more complete understanding of the present invention and the advantages thereof, reference is now made to the following description taken in connection with the accompanying drawings, in which.

DETAILED DESCRIPTION OF THE INVENTION

Embodiments of the present invention and the advantages thereof are best understood by referring to the following descriptions and drawings, wherein like numerals are used for like and corresponding parts of the drawings.

Figure 1:
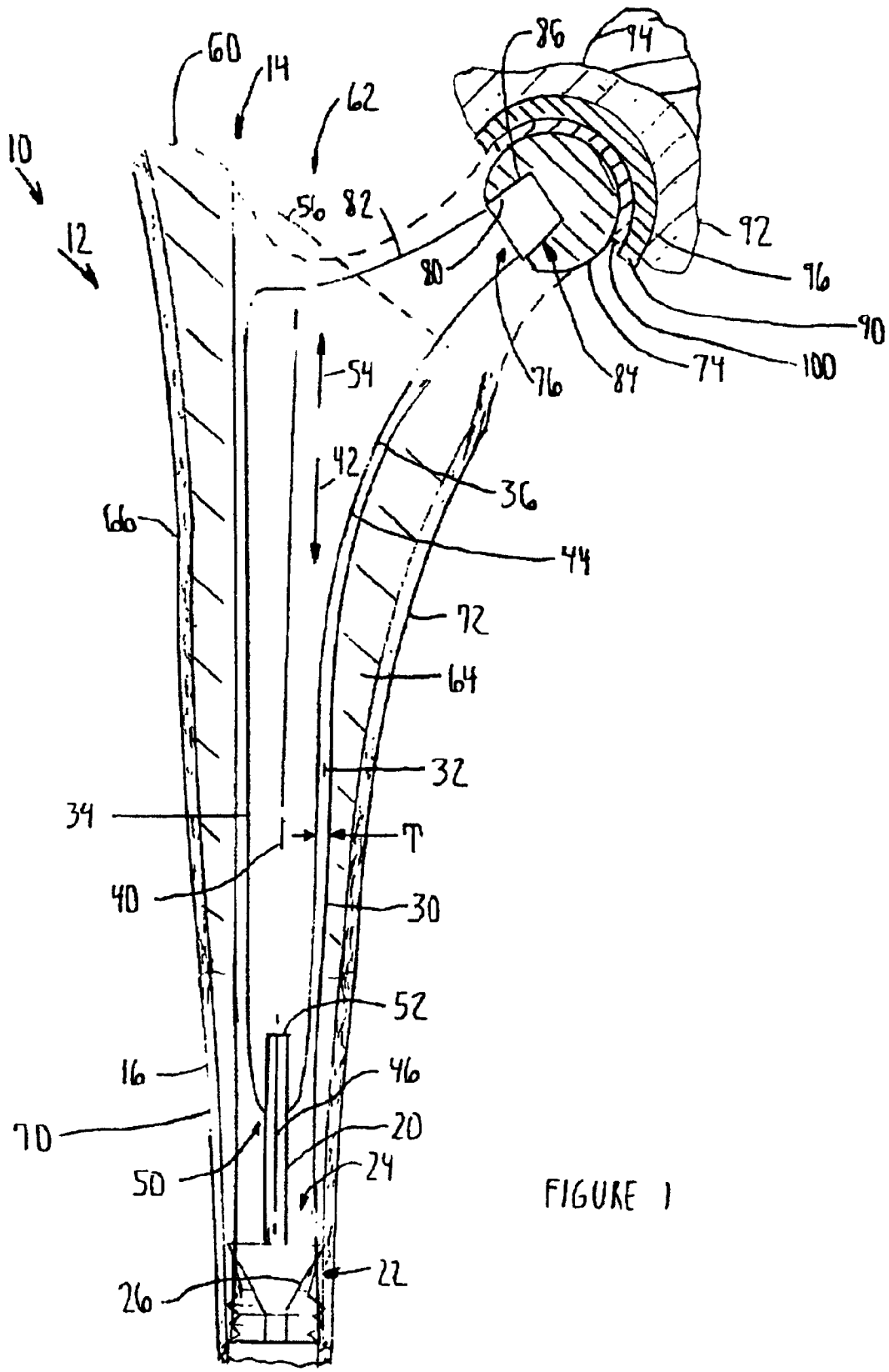
FIG. 1 is a plan view of a hip prosthesis implanted into a femur and an acetabulem with a centralizer in accordance with an embodiment of the present invention.

According to the present invention and referring to FIG. 1, prosthesis 10 is shown. The prosthesis 10 includes a stem 12. The stem 12 is used for implantation at least partially within medullary canal 14 of long bone or femur 16. The prosthesis 10 also includes a rod 20. The rod 20 is operably associated with the stem 12. The prosthesis 10 further includes a centralizer 22. The centralizer 22 defines an aperture or opening 24 within the centralizer 22. The aperture 24 serves to receive at least a portion of the rod 20. The centralizer 22 includes a surface 26 of the centralizer 22 for guiding the rod 20 into the aperture 24.

The stem 12 may have any suitable shape to provide for a durable prosthesis. The stem 12 may have a shape adapted to provide controlled subsidence of the stem 12 into cement mantle 30 formed by cement 32 around the stem 12. While a variety of shapes of the stem 12 may provide for controlled subsidence of the stem 12, the stem 12 of the prosthesis 10 may include a distal portion or first portion 34 and a body portion or second portion 36. The first portion 34 is operably connected to the second portion 36.

For example to provide for pressure on the stem 12, the width of the body portion 36 may steadily decrease in both the medial/lateral and anterior/posterior directions in a direction along axis 40 in the direction of arrow 42. The decreasing width of the stem 12 in the direction of arrow 42 in combination with load applied to the prosthesis 10 in the direction of arrow 42 provides continual pressure on the cement mantle 32 and serves to promote bone growth and reduced osteolysis.

The stem 12 may be made of any suitable or durable material which is biocompatible and clinically proven. For example, the stem 12 may be made of a durable metal, for example a cobalt chromium alloy, a stainless steel alloy, titanium or a titanium alloy.

Outer periphery 44 of the stem 12 may have a surface finish which is conducive to permitting cement creep and controlled subsidence. The outer periphery 44 of the stem 12 may be polished.

The rod 20, as shown in FIG. 1, may define a rod longitudinal axis 46. The first portion or distal portion 34 of the stem 12 may define a cavity 50 of the stem 12. A first end 52 of the rod 20 may be fitted within cavity 50 of the stem 12. As shown in FIG. 1, the rod 20 may be removable from the stem 12 in the direction of arrow 42 along the axis 40 of stem 12. Similarly, the rod 20 may be restrained within the stem 12 along direction of arrow 54 opposed to the direction of arrow 42 along the axis 40 of stem 12.

The rod 20 may have any suitable shape which is suitable to interconnect the stem 12 to the centralizer 22. As shown in FIG. 1, the rod 20 may be elongated in the directions of arrows 42 and 54 and may, as shown in FIG. 1, have a uniform cross-section. For example, the rod 20 may have a circular cross-section. It should be appreciated, however, that the rod 20 may have any of a variety of polygon or any odd shaped cross-sectional shape. The rod 20 may be made of any suitable, durable, biocompatible material. For example, the rod 20 may be made of a metal or a plastic. The rod 20 may also be made of bone cement material, for example, polymethylmethacrylate (PMMA) 04 a bioresorbable material.

The method for inserting a prosthesis 10 to perform a total hip arthroplasty is generally well known. To perform a total hip arthroplasty, the patient's skin is cut to expose the femur 16. The femur 16 is resected along resection line 56 separating epiphysis 60 from the femur 16. The epiphysis 60 is shown as a dashed line.

The prosthesis 10 is implanted into the femur 16 by positioning the prosthesis 10 into opening or cavity 62 formed by, for example, drilling, reaming or broaching a portion of the medullary canal 14 made up of cancellous bone 64 of the femur 16.

The cavity 62 may be formed in the cancellous bone 64 of the medullary canal 14 by either broaching or reaming or other similar techniques to remove the cancellous bone 64 from the canal 14. As shown in FIG. 1, the cavity 62 extends from metaphysis 66 into diaphysis 70 of the femur 16.

As shown in FIG. 1, the prosthesis 10 is preferably utilized with bone cement 32 which forms cement mantle 30 over outer periphery 44 of the body portion 36 and the distal portion 34 of the stem 12. The cement mantle 30 has a thickness T of, for example, 0.5 to 4.5 millimeters.

Any suitable combination of drilling, reaming or broaching can be used to form the cavity 62 which corresponds closely to the periphery of the prosthesis 10 but yet accounts for the thickness T of the cement mantle 30. Typically, after drilling and perhaps reaming, a broach (not shown) is driven into the medullary canal to form the cavity 62. This broach has a shape generally larger than the portion of the implant that fits into the canal 62 so that the prosthesis may be spaced from the canal 62 by the thickness T of the cement mantle 30.

The cavity 62 is formed a sufficient size to provide for the positioning of the stem 12 and the presence of the cement mantle 30 between the stem 12 and the cancellous bone 64. The outer hard portion of the long bone, commonly known as cortical bone 72, is preferably not or minimally reamed or broached to form the opening 62.

As shown in FIG. 1, the prosthesis 10 may further include a head 74 which is operably associated with the stem 12. The head 74 may be operably associated with the stem 12 in any suitable manner. For example, the head 74 may include a cono-frustical recess 76 forming an internal tapered surface 80.

As shown in FIG. 1, the stem 12 may include a neck portion 82 extending proximally in the direction of arrow 54. The neck portion 82 may include an externally tapered portion 84 having an external surface 86. As shown in FIG. 1, the external surface 86 of the portion 84 of the neck 82 is matingly fitted to internal surface 80 of the head 74.

The prosthesis 10 may further include a cup 90 for pivotal engagement with the head 74. The cup 90 may be secured to acetabulum 92 of hip 94 in any suitable fashion. For example, the cup 90 may include a hemispherical outer surface 96 which matingly fits with acetabulum 92 of the hip 94. The outer surface 96 of the cup 90 may include openings (not shown) to which fasteners (not shown) are fitted for securement to the acetabulum 92 or may include a threaded periphery (not shown) for engagement with the acetabulum 92.

The cup 90 may be in pivotal engagement with the head 74 in any suitable fashion. For example, the head 74 and the cup 90 may have mating surfaces for metal to metal contact with each other or, as shown in FIG. 1, a liner 100 may be pivotally located between the cup 90 and the head 74.

The liner 100 may be made of a durable metal, a ceramic, or be made of a nonmetallic material, for example, a plastic. For example, the liner 100 may be made of a high molecular weight polyethylene. For example, the liner 100 may be made of ultrahigh molecular weight polyethylene. One particular ultrahigh molecular weight polyethylene that is well suited for this application is sold by DePuy Orthopaedics, Inc. as Marathon® and is generally described in U.S. Pat. Nos. 6,017,975 and 6,228,900 which are hereby incorporated by reference in their entireties.

Figure 2:
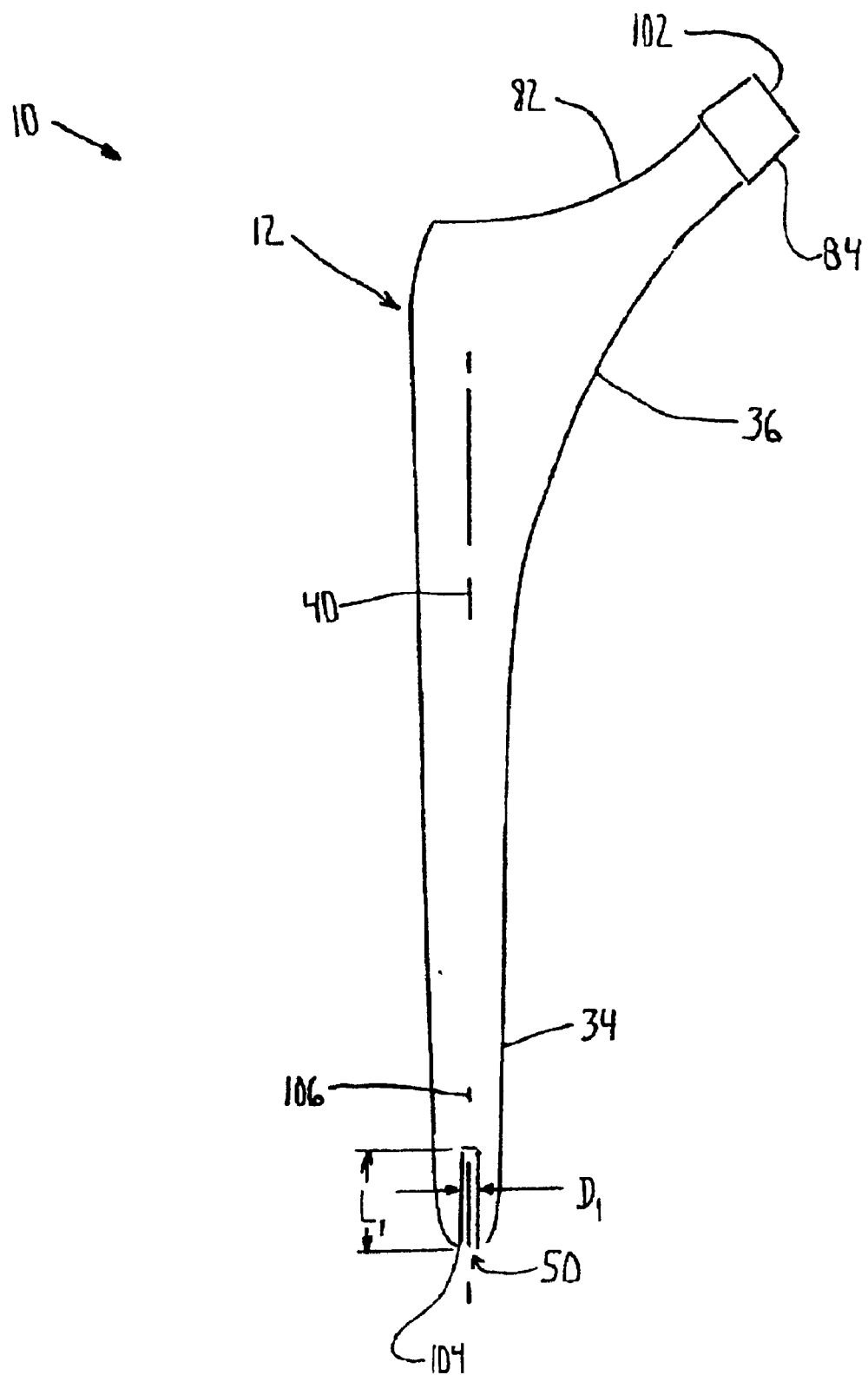
FIG. 2 is a plan view of hip stem for use in the hip prosthesis of FIG. 1.

Referring now to FIG. 2, the stem 12 of the prosthesis 10 is shown in greater detail. As shown in FIG. 2, the stem 12 extends from proximal end 102 to distal end 104. As shown in FIG. 2, the stem 12 includes an external tapered portion 84 located at proximal end 102. Extending distally from the external tapered portion 84 is the neck portion 82. Extending distally from the neck portion 82 is the body portion 36. Extending distally from the body portion 36 is the distal portion 34.

The cavity 50 may have any suitable shape that serves to provide for a connection of the rod 20 (see FIG. 1). For example, for a rod 20 having a cylindrical shape, the cavity 20, as shown in FIG. 2, has a cylindrical shape having a diameter $D_1$ and a length extending proximally from distal end 104 of $L_1$. As shown in FIG. 2, the cavity 50 may have a cavity centerline axis 106 which is coincident with centerline axis 40 of the stem 12.

Figure 3:
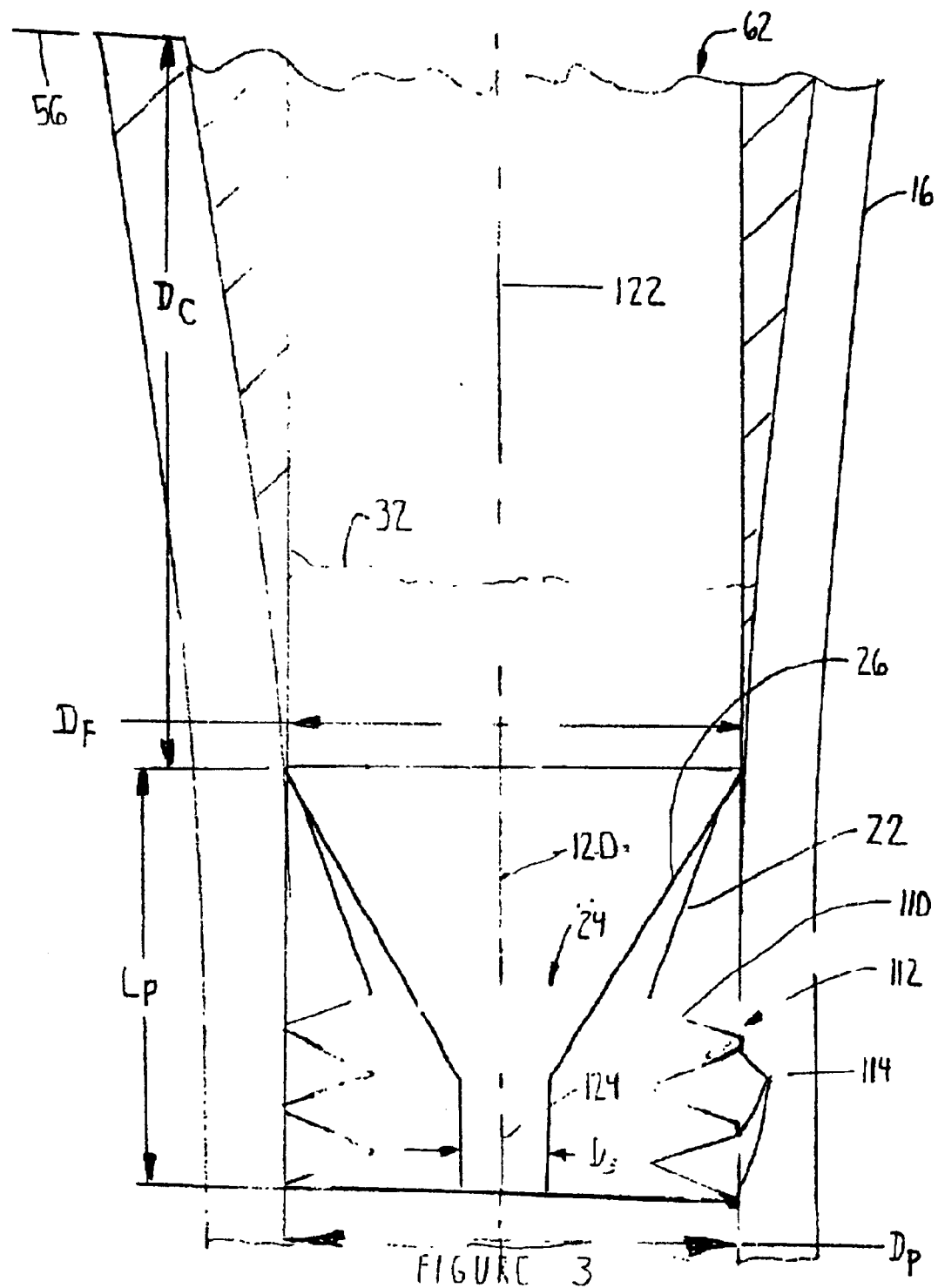
FIG. 3 is a partial enlarged plan view of a ceentralizer for use with the hip prosthesis of FIG. 1 showing the centralizer in greater detail.

Referring now to FIG. 3, the centralizer 22 is shown installed in opening 62 of the femur 16. While it should be appreciated that the invention may be practiced with the centralizer 22 pre-assembled to the rod 20 and inserted into the opening and the stem later mated to the rod to form the prosthesis, and while it should be appreciated that the stem 12, rod 20 and centralizer 22 may all be pre-assembled and inserted into the opening 62, preferably, the centralizer 22 is first positioned in the opening 62 as shown in FIG. 3.

The centralizer 22 may be made of any suitable durable material which is biocompatible with the human body. For example, the centralizer 22 may be made of a plastic, for example, polyethylene or polymethylmethacrylate (PMMA).

The centralizer 22 may have any shape which is compatible with the opening or cavity 62 so that the centralizer 22 may be securely positioned within the opening or cavity 62. For example and as shown in FIG. 3, the centralizer 22 may have a generally cylindrical shape and may have a diameter $D_P$ and a length $L_P$. The centralizer 22 has an outer periphery 110 which preferably conforms to opening or cavity 62.

While the outer periphery 110 may be generally cylindrical to conform to the cavity 62, the outer periphery 110 may include reduced contact areas 112 which provide for reduced contact between the centralizer 22 and the opening 62. The reduced contact areas 112 may be in the form of, for example, tips or fins 114 which extend outwardly from the centralizer 22. The centralizer 22 may have a solitary fin 114 or may, as shown in FIG. 3, include a plurality of fins 114.

The fins 114 may have any shape and may, as shown in FIG. 3, be, for example, generally rectangular or triangular in cross-section. The fins 114 may be placed in a helical fashion about the outer periphery 110 of the centralizer 22 or may be in the form of spaced apart annular rings. The utilization of reduced contact areas 112 may provide for improved sealing of the blood and bone marrow distally to the centralizer 22.

The centralizer 22, as earlier stated, includes the surface 26 which is utilized for guiding the rod 20 (see FIG. 1) into the aperture 24. Preferably and as shown in FIG. 3, the surface 26 converges toward the aperture 24. The surface 26 may in fact be cono-frustical or in the shape of a funnel. When the surface 26 has a cono-frustical shape, the surface 26 is defined by flared diameter $D_F$ and diameter $D_3$ located at distal end of the centralizer 22.

Preferably and as shown in FIG. 3, the aperture 24 of the centralizer 22 defines a through hole for the passage there through of at least a portion of the rod 20 (see FIG. 2).

When performing an arthroplasty after the opening or cavity 62 has been fully broached, the centralizer 22 is positioned into the opening 62 with surface 26 positioned proximally in the cavity 62. The centralizer 26 is positioned into the cavity 62 a distance $D_C$ from the resection plane 56. The outer periphery 110 of the centralizer 22 serves to position the centralizer with the centralizer centerline axis 120 being coincident with cavity centerline axis 122. Preferably and as shown in FIG. 3, the aperture 24 of the centralizer 22 has an aperture centerline axis 124 which is coincident with the centralizer centerline axis 120 and the cavity centerline axis 122.

Figure 4:
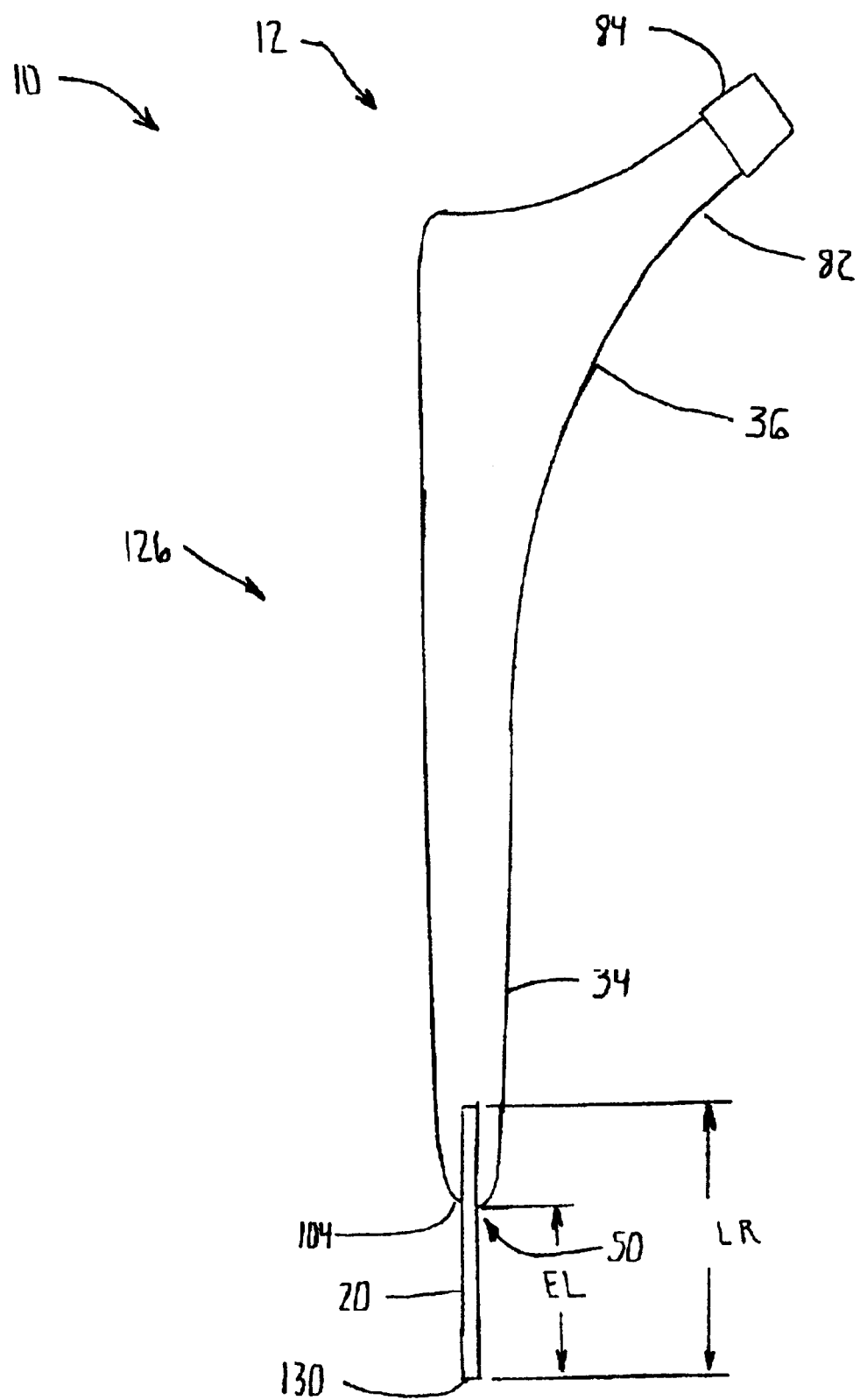
FIG. 4 is is a plan view of the hip stem of FIG. 2 with a rod installed in the tip thereof.

Referring now to FIG. 4, the stem 12 of the prosthesis 10 is shown with the rod 20 attached to the distal end 104 of the stem 12. Preferably, the rod 20 is pre-assembled into the distal end 104 of the stem 12. The rod 20 extends a distance $E_L$ from the distal end 104 of the stem 12 with a portion of the length $L_R$ of the rod 20 positioned within cavity 50 of the distal portion 34 of the stem 12.

Preferably the rod 20 is fixably secured to the stem 12. The rod may be fixably secured to the stem 12 by an interference fit, threads, or any other suitable method of attachment, including for example, an adhesive. The stem 12 and the rod 20 thus form stem and rod assembly 126.

Figure 5:
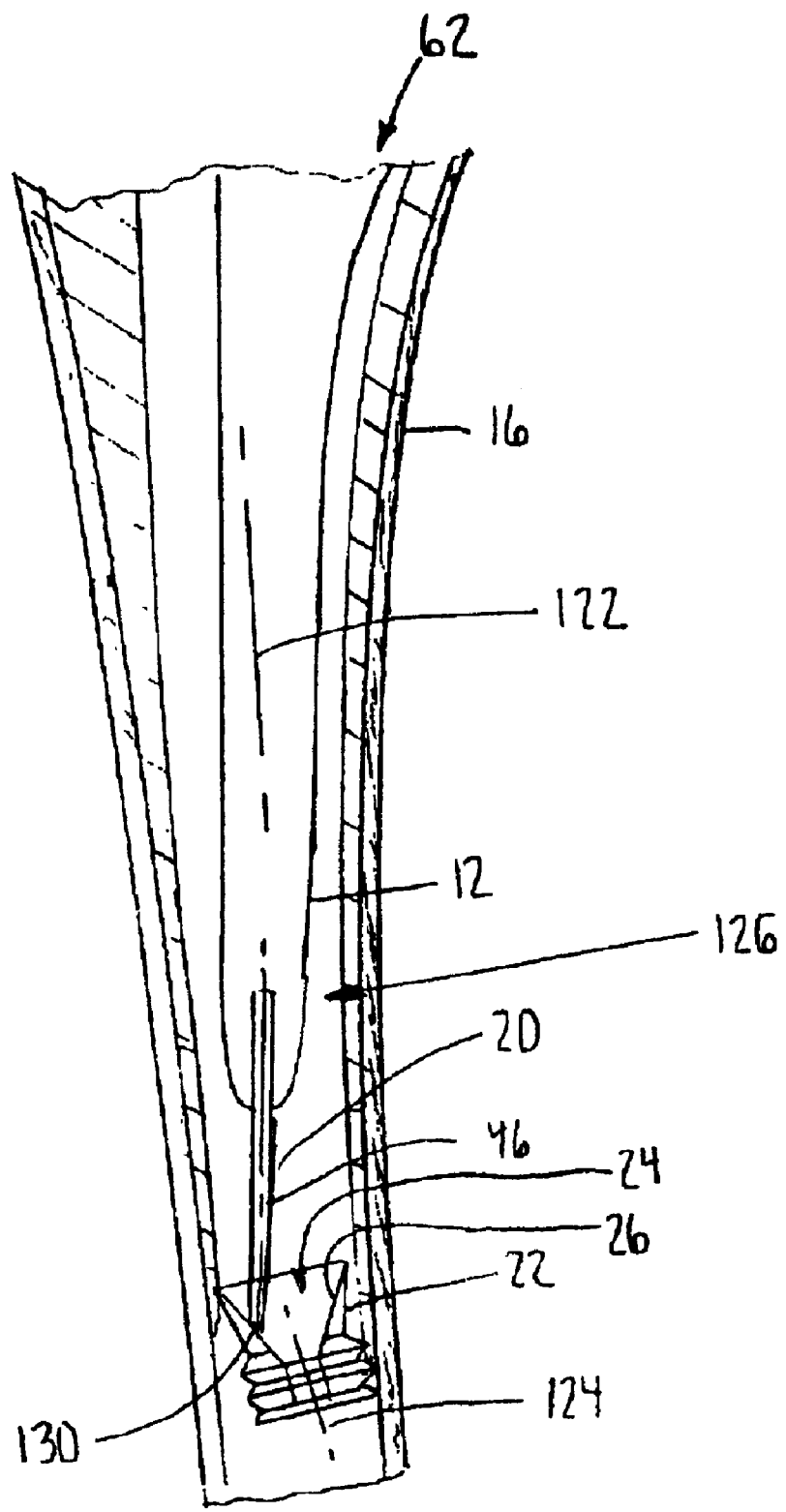
FIG. 5 is a partial plan view of the hip prosthesis of FIG. 1 showing the stem and rod assembly of FIG. 4 being installed into a centralizer which is mis-positioned.

Referring now to FIG. 5, the stem and rod assembly 126 is shown partially inserted into opening 62 of the femur 16. As shown in FIG. 5, even if the stem and rod assembly 126 is inserted with the rod centerline 46 skewed with respect to the cavity centerline axis 122, and if the centralizer aperture centerline axis 124 is skewed with respect to the cavity centerline axis 122, the distal tip 130 of the rod 20 contacts the surface 26 of the centralizer 22 and the centralizer 22 guides the distal tip 130 of the rod 22 into the aperture 24 of the centralizer 22 thereby aligning the rod 20 and the centralizer 22 such that their respective centerlines become co-existent.

Figure 6:
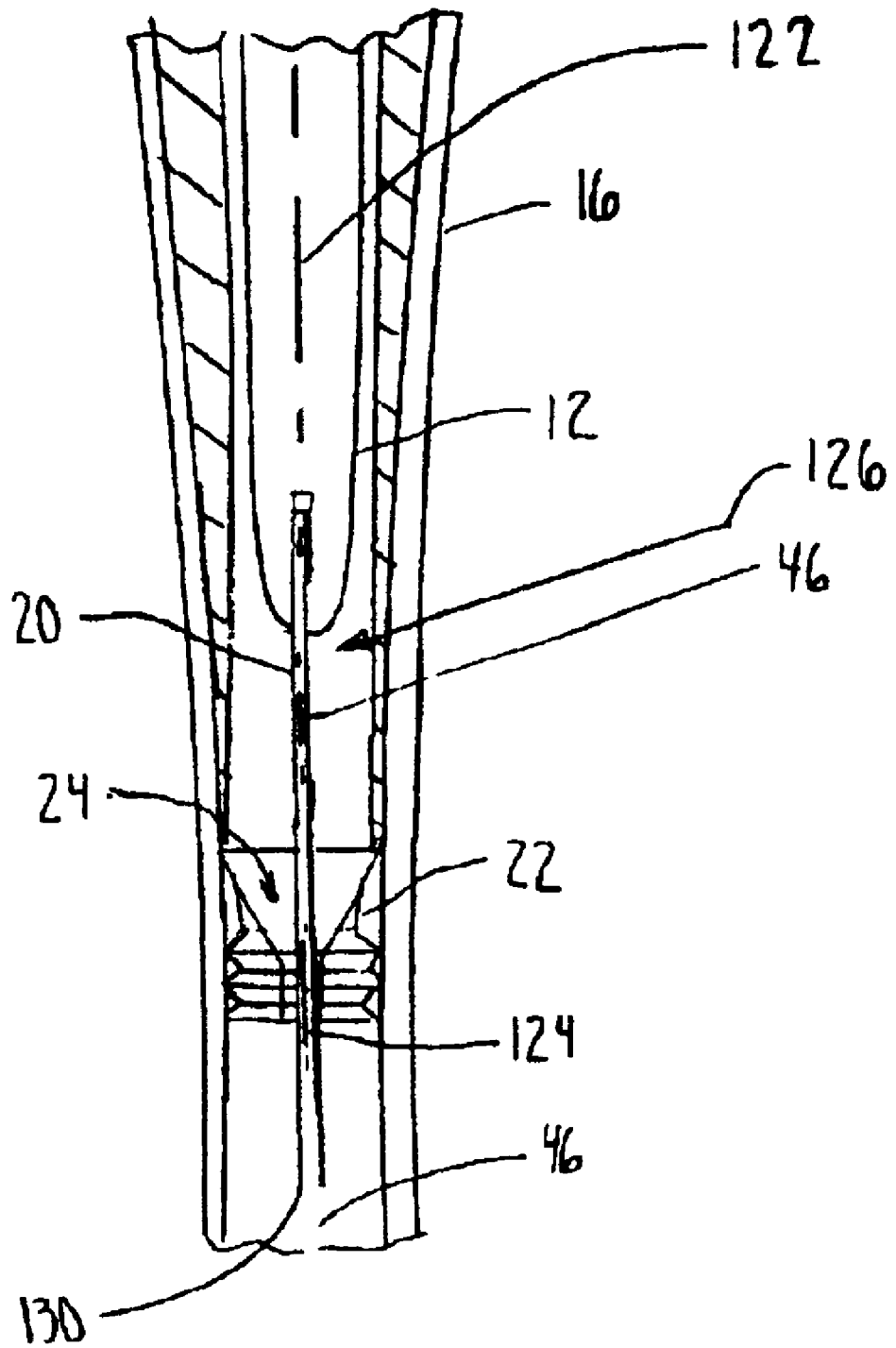
FIG. 6 is a partial plan view of the hip prosthesis of FIG. 1 showing the rod passing through the centralizer.

Referring now to FIG. 6, the stem and rod assembly 126 is shown with the rod 22 fully inserted through the aperture 24 of the centralizer 22 such that the centerline axis 46 of the rod 20 and the centralizer aperture axis 124 of the centralizer 22 are coincident with the cavity centerline axis 122 and the rod 20 and centralizer 22 are in their proper position within the opening 62.

Figure 7:
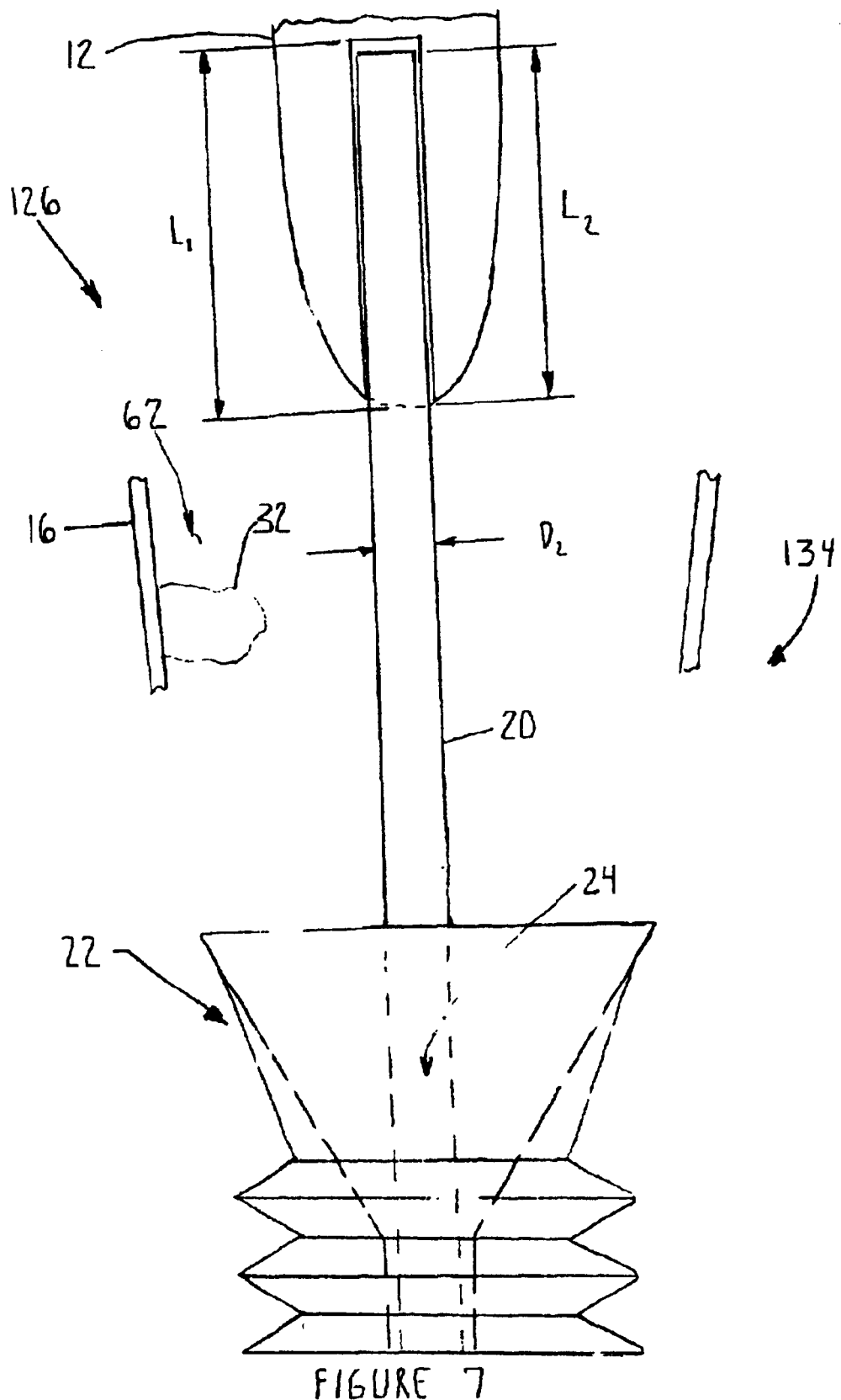
FIG. 7 is a partial plan view of the prosthesis of FIG. 1 showing the rod, stem opening and centralizer in greater detail.

Referring now to FIG. 7, the stem and rod assembly 126 is shown with the rod 20 fully inserted through aperture 24 of the centralizer 22 so as to form stem, rod and centralizer assembly 134. With the stem, rod and centralizer assembly 134 finally positioned in the opening 62 of the femur 16, the cement 32 is securely and completely filling the aperture or opening 62 proximally of the centralizer 22 subsequent to the installation of the centralizer 22. Pressure may now be applied at the resection plane 56 (see FIG. 1) to the cement 32 so as to remove any remaining voids within the cement 32.

Figure 8:
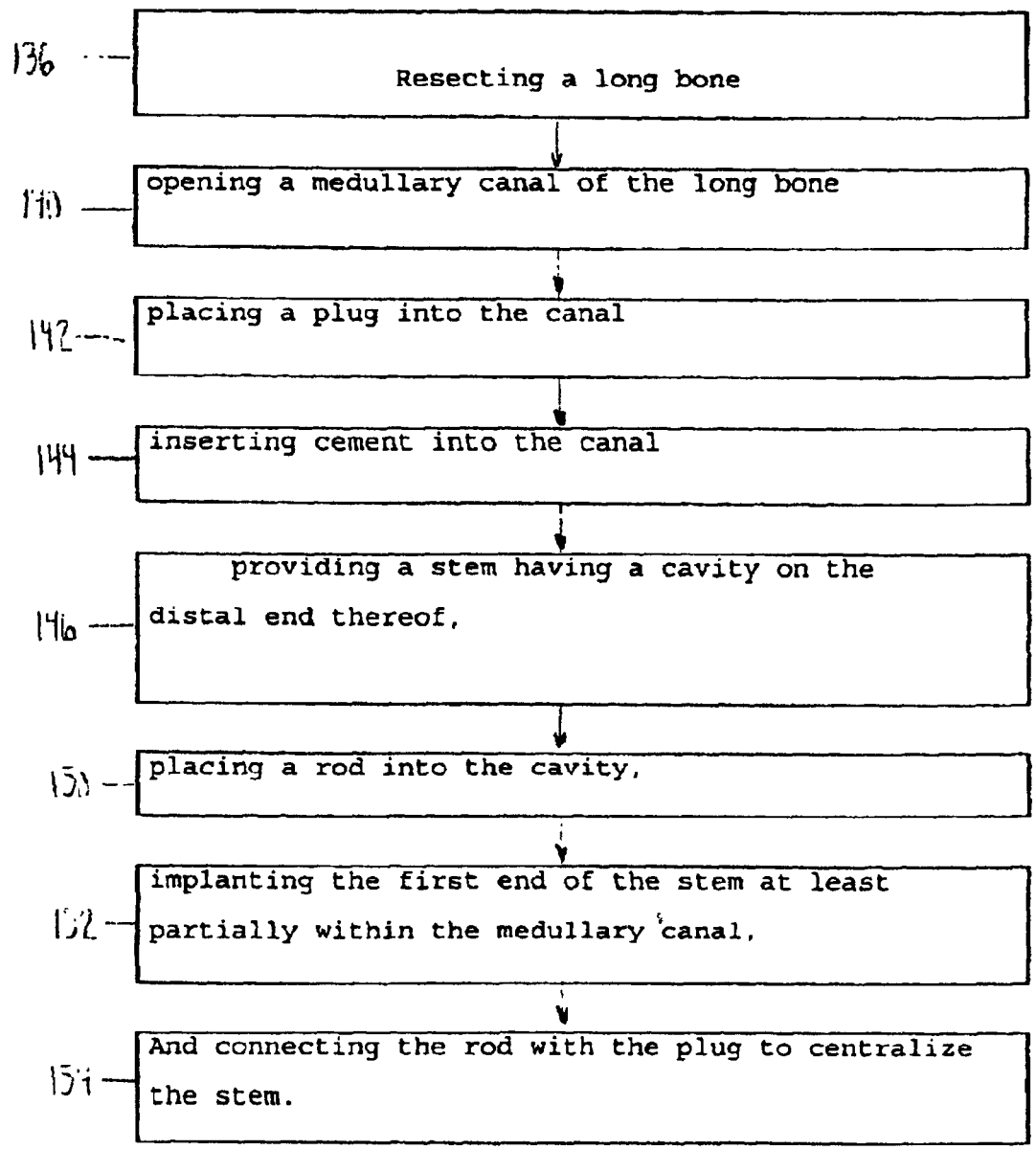
FIG. 8 is a flow chart of a method of performing arthroplasty according to the present invention.

Referring now to FIG. 8, a method for providing total hip arthroplasty is shown. The method includes the first step 136 of resecting a long bone. The method further includes a second step 140 of opening a medullary canal of the long bone. The method also includes a third step 142 of placing a plug into the canal. The method also includes a fourth step 144 of inserting cement into the canal. The method further includes a fifth step 146 of providing a stem having a cavity on the distal end thereof. The method also includes a six step 150 of placing a rod into the cavity. The method further includes a seventh step 152 of implanting the first end of the stem at least partially within the medullary canal. The method also includes the eighth step of connecting the rod with the plug to centralize the stem.

Figure 9:
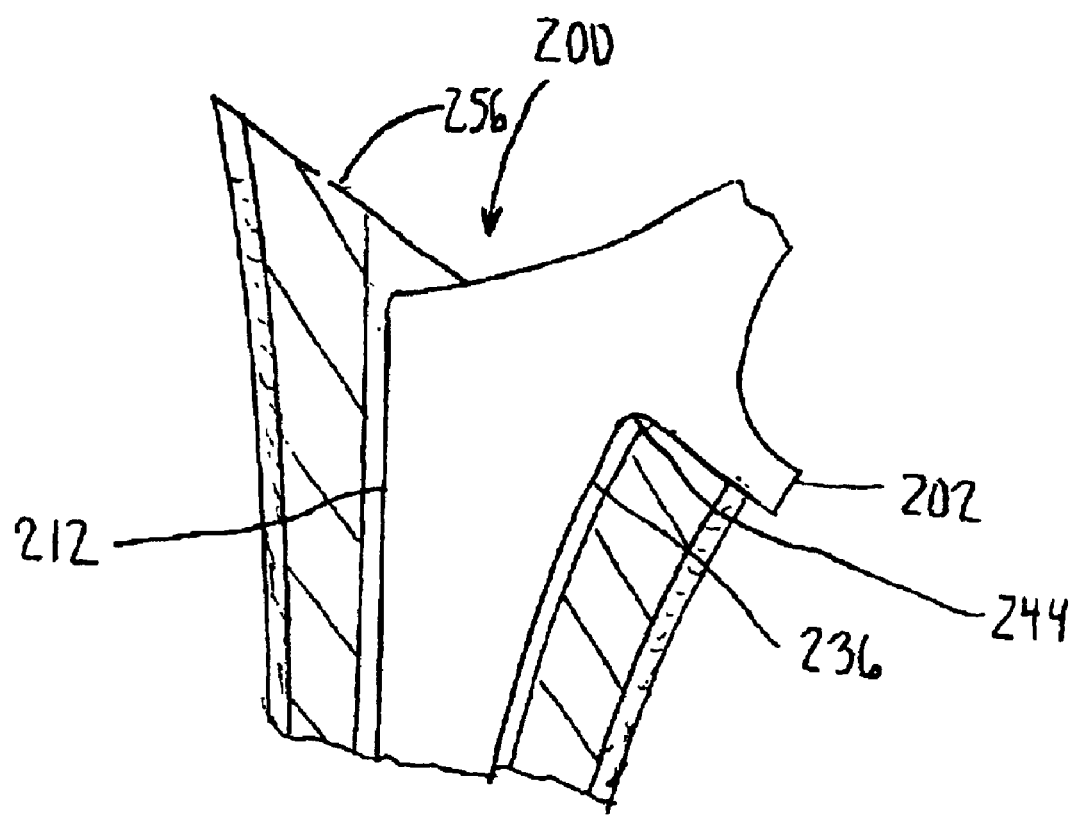
FIG. 9 is a partial plan view of an alternate embodiment of the present invention showing a stem with a collar.

Referring now to FIG. 9, the prosthesis according to the present invention may alternatively be in the form of prosthesis 200 which includes a stem 212 which is similar to stem 12 of the prosthesis 10 of FIG. 1 except that stem 12 has a collar 202. The collar 202 extends outwardly from outer periphery 244 of the body portion 236 of the stem 212. The collar 202 is positioned above resection plane 256 and is used to assist in supporting the prosthesis 200 and compressing the cement.

By providing a prosthesis including a rod extending from a stem, stem centralization may be accomplished with use of a cement restrictor.

By providing a cement plug which is flared at its proximal end, a distal rod may be guided into the center of the canal creating a uniform cement mantle around the stem.

By providing a cement restrictor having centralizing features and thereby having a distal centralizer which does not have fins, smooth cement flow is capable around the distal tip of the stem reducing the formation of voids in the cement mantle.

By providing a cement plug with a through hole, a rod positioned distally in the stem may pass through the cement plug without pushing it out of position. This permits some malpositioning of the cement plug within the canal.

Although the present invention and its advantages have been described in detail, it should be understood that various changes, substitutions, and alterations can be made therein without departing from the spirit and scope of the present invention as defined by the appended claims.

What is claimed is:

1. A prosthesis comprising:
   a stem for implantation at least partially within the medullary canal of a long bone;
   a rod connected to said stem and extending therefrom; and
   a centralizer defining an aperture therethrough for slidably receiving at least a portion of said rod, said rod and said centralizer closely conforming to each other during the slidable receiving thereof, said centralizer including a surface thereof for guiding said rod into the aperture, wherein said stem has a first portion and a second portion, said first portion defining an cavity therein; andwherein said rod defines a longitudinal axis thereof, said rod being removable from the stem a first direction along the axis and said rod being restrained within said stem a second direction opposed to the first direction along the axis.

2. A prosthesis comprising:
   a stem for implantation at least partially within the medullary canal of a long bone, said stem having a first portion and a second portion, said first portion defining an cavity therein;
   a rod connected to said stem and at least partially fittable within the cavity of the first portion of said stem, said rod defining a longitudinal axis thereof, said rod being removable from the stem a first direction along the axis and said rod being restrained within said stem a second direction opposed to the first direction along the axis; and
   a centralizer defining an opening therein, the opening of said centralizer and said rod having a closely conforming fit therebetween during the relative motion therebetween.

3. The prosthesis of claim 2, wherein said centralizer defines a aperture therein for receiving at least a portion of said rod, said centralizer including a surface thereof for guiding said rod into the aperture.

4. The prosthesis of claim 2, wherein the surface of said centralizer for guiding said rod into the aperture converges toward the aperture.

5. The prosthesis of claim 4, wherein the surface of said centralizer for guiding said rod into the aperture comprises a funnel.

6. The prosthesis of claim 2, wherein the aperture of said centralizer comprises a through hole for the passage therethrough of at least a portion of said rod.

7. The prosthesis of claim 2 wherein said centralizer comprises ribs on the outer periphery thereof.

8. The prosthesis of claim 2, wherein at least one of said rod and said centralizer comprises a resorbable material.

* * * * *